United States Patent [19]

Stahl et al.

[11] 4,127,386
[45] Nov. 28, 1978

[54] PROCESS AND SYSTEM FOR MEASURING SULFUR DIOXIDE POLLUTION

[75] Inventors: Quade R. Stahl, Springfield, Va.; Joseph H. Ney, Rockville, Md.

[73] Assignee: Meloy Laboratories, Inc., Springfield, Va.

[21] Appl. No.: 762,736

[22] Filed: Jan. 26, 1977

[51] Int. Cl.$^2$ ............................................. G01N 31/06
[52] U.S. Cl. ................................. 23/232 R; 423/230; 422/88
[58] Field of Search ............... 423/224, 230, 561, 566; 55/73 (U.S. only); 23/230 L (U.S. only), 232 R (U.S. only), 254 R

[56] References Cited

U.S. PATENT DOCUMENTS

| | | | |
|---|---|---|---|
| 1,770,694 | 7/1930 | Henninger | 23/232 R |
| 3,579,305 | 5/1971 | Neti | 23/232 R |
| 3,847,552 | 11/1974 | Hobgood et al. | 23/232 R |

OTHER PUBLICATIONS

Levaggi et al., Technique for Increasing the Specificity of the Titrilog, American Chemical Society Papers, 1961, p. 6W.
Natusch et al., Sensitive Method for Measurement of H$_2$S, Analytical Chemistry, 1972, pp. 2067–2070.
Jacobson, Encyclopedia of Chemical Reactions, vol. VI, 1956, p. 237.

*Primary Examiner*—O. R. Vertiz
*Assistant Examiner*—Thomas W. Roy
*Attorney, Agent, or Firm*—Shapiro and Shapiro

[57] ABSTRACT

Hydrogen sulfide scrubber for use with sulfur compound analyzers effectively removes hydrogen sulfide from gas streams, such as ambient air, without removing substantial amounts of other sulfur compounds, particularly sulfur dioxide. The scrubber employs a bed of silver sulfate, silver nitrate, or silver iodide and operates effectively over wide temperature and humidity ranges without requiring temperature control, with minimal interference from ozone, and operates at flow rates employed by conventional sulfur analyzers without excessive pressure drops.

9 Claims, 2 Drawing Figures

PROCESS AND SYSTEM FOR MEASURING SULFUR DIOXIDE POLLUTION

BACKGROUND OF THE INVENTION

This invention is concerned with the selective removal of hydrogen sulfide from gas streams containing other sulfur compounds, especially sulfur dioxide.

Regulations of the United States Government concerning ambient air monitoring require that sulfur dioxide be measured without hydrogen sulfide interference. Prior methods employ elemental silver, usually in the form of wool or gauze, which must be heated to about 140° C. to permit the passage of sulfur dioxide while removing hydrogen sulfide. Such methods suffer from ozone interference, require closely maintained temperature control, are unduly expensive, and are difficult to implement.

BRIEF DESCRIPTION OF THE INVENTION

It is a principal object of the present invention to provide an improved method and an improved device for the selective removal of hydrogen sulfide from gas streams, particularly for the removal of hydrogen sulfide while passing sulfur dioxide, although carbon disulfide and carbonyl sulfide are among other sulfur compounds which it may be desired to pass.

A further object of the invention is to provide effective hydrogen sulfide scrubbing which does not require temperature control (although temperature control may be used), which operates without substantial interference from ozone or other common air pollutants, such as $CH_4$, $C_2H_2$, $C_2H_4$, $H_2O$, $NO$, $NO_2$, $CO$, or $CO_2$, which employs a material which is less expensive than pure silver, which does not require pre-treatment of the scrubbing material, which operates effectively over wide temperature and humidity ranges, which operates at conventional flow rates employed by sulfur analyzers or monitors without excessive pressure drops, and in which the scrubbing device is easily adapted to various configurations and sizes and requires less production time to manufacture.

Briefly stated, the invention is based upon the surprising discovery of the remarkable ability of certain silver compounds — namely, silver sulfate, silver nitrate and silver iodide — to remove hydrogen sulfide selectively from a gas stream operated under typical ambient temperatures and humidity. More specifically, a preferred embodiment of the invention employs silver sulfate crystals as a bed in a tubular reactor through which the gas stream is passed to a sulfur analyzer including a flame photometric detector.

BRIEF DESCRIPTION OF THE DRAWINGS

The invention will be further described in conjunction with the accompanying drawings, which illustrate preferred and exemplary embodiments, and wherein.

DETAILED DESCRIPTION OF THE INVENTION

The present invention is based upon the surprising discovery that certain compounds of silver — namely, silver sulfate, silver nitrate and silver iodide — may be effectively employed in an appropriately constructed scrubber to remove almost all of the hydrogen sulfide in a gas stream while passing almost all of the sulfur dioxide in the gas stream, as well as other sulfur compounds, the selective removal of hydrogen sulfide being effective over a wide operating temperature range without requiring temperature control, over a wide range of relative humidity, and with minimal interference from ozone or other substances which commonly cause interference. A hydrogen sulfide scrubber in accordance with the invention is simple and compact and operates at conventional flow rates employed by sulfur analyzers without excessive pressure drops and over a long useful life. Surprisingly, the performance of the invention cannot be achieved, and in most instances cannot even be approached, with other commonly available silver compounds, including silver tungstate, silver tetrafluoroborate, silver oxide, silver chromate, silver acetate, silver sulfide, silver thiocyanate, silver phosphate, silver citrate, silver oxalate, silver sulfite, silver carbonate, and silver bromate.

These compounds have been found to suffer from one or more of the following deficiencies:

(1) inadequate removal of hydrogen sulfide;
(2) inadequate passage of sulfur dioxide;
(3) inadequate lifetime;
(4) intolerable sensitivity to ozone and other interfering substances;
(5) slow response or long recovery time;
(6) erratic peaking effects; and
(7) hydroscopic properties or corrosiveness.

Preferred embodiments of the invention will now be described.

Figure 1:
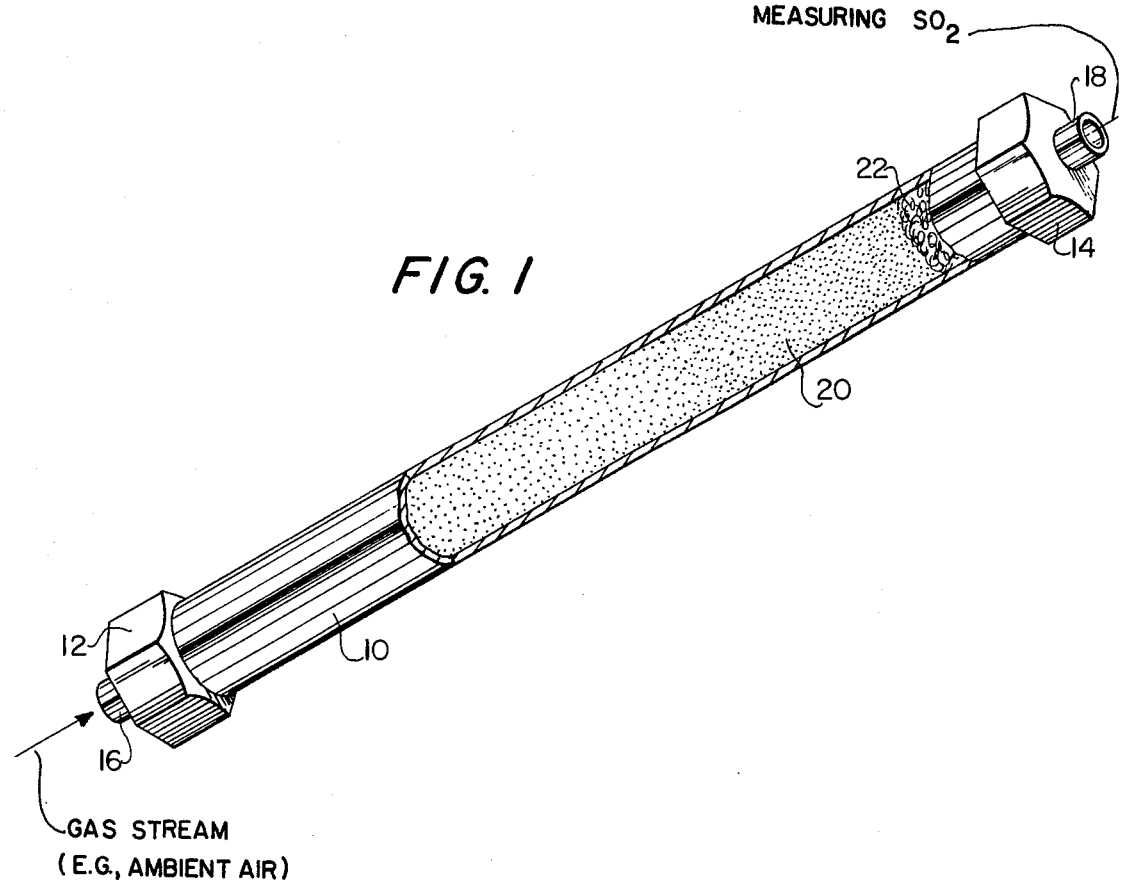
FIG. 1 is a partly sectional perspective view illustrating a scrubbing device in accordance with the invention.

In a first example of the invention, illustrated in FIG. 1, a scrubber comprises a tube 10 of Teflon, stainless steel, or other inert material having inlet and outlet fittings 12 and 14, respectively, similarly of inert material. The ends of the tube may be threaded and tapered to receive the fittings, which may be of the Swagelok type, for example, and which permit coupling of the tube 10 to inlet and outlet pipes 16 and 18, respectively. In the embodiment of FIG. 1 tube 10 is about 3 inches long and has an inner diameter of about ¼-inch. ⅛th-inch diameter inlet and outlet pipes may be employed, also of inert material.

In accordance with the first example of the invention, tube 10 contains a hydrogen sulfide scrubber bed 20, preferably about 4–6 grams of about 10–30 mesh silver sulfate crystals which fill the tube except for gas-dispersing, crystal-retaining plugs 22 at opposite ends of the tube (only one plug being illustrated in FIG. 1). The plugs are formed of glass wool, for example, or of similar inert material. The effective length of the bed of silver sulfate crystals is about 2½ inches. The packing density is not critical, although too tight packing could result in high pressure drops. A plug 22 may be installed in one end of the tube 10 and the crystals poured into the opposite end while the tube is tapped to distribute the crystals uniformly and to avoid the possibility of "channeling" by the sample or feed gas. When the tube 10 is almost full, the other plug 22 is installed. At the flow rates employed in commercially available sulfur analyzers and monitors such as the Model SA185-2 or the Model SA285 sulfur analyzers of Meloy Laboratories, Inc., 200 ± 20cc/min, the pressure drops are quite acceptable (not excessive) when the crystals merely fill the reactor space without additional tamping. The active reactor volume in the example is approximately 0.14 cubic inches.

In use, outlet 18 is connected to a suitable sulfur analyzer or monitor, such as the type referred to above including a flame photometric detector for measuring the concentration of sulfur compounds such as sulfur dioxide. A gas stream, such as ambient air, is supplied to inlet 16 by a vacuum pump associated with the measuring instrument (or by a positive pressure source). In the example, with a sample gas flow rate of 200 ± 20cc/min., at least about 98% of the hydrogen sulfide is removed from the gas stream in the concentration range of zero to 1ppm, while at least about 98% of the sulfur dioxide is passed. The invention operates over a temperature range of at least about 10°–40° C. and a relative humidity range of at least 10–95%. Useful life is approximately 90ppm $H_2S$ hours (e.g., 900 hours with 0.1ppm $H_2S$ sample drawn through at 200cc/min). Accurate measurement of $SO_2$ (and other sulfur compounds) is achieved without $H_2S$ interference and with minimal interference from ozone and other common air pollutants. Temperature control is not required if the operating range is 10°–40° C. No pretreatment of the silver sulfate scrubbing material before insertion into its holder is required. The scrubbing device of the invention can be manufactured rapidly and economically and is easily adapted to various configurations and sizes to meet special design requirements. Of course, the bed dimensions depend somewhat upon the flow rate of the sample gas, the surface area of the crystals, and the desired useful life of the scrubber.

Figure 2:
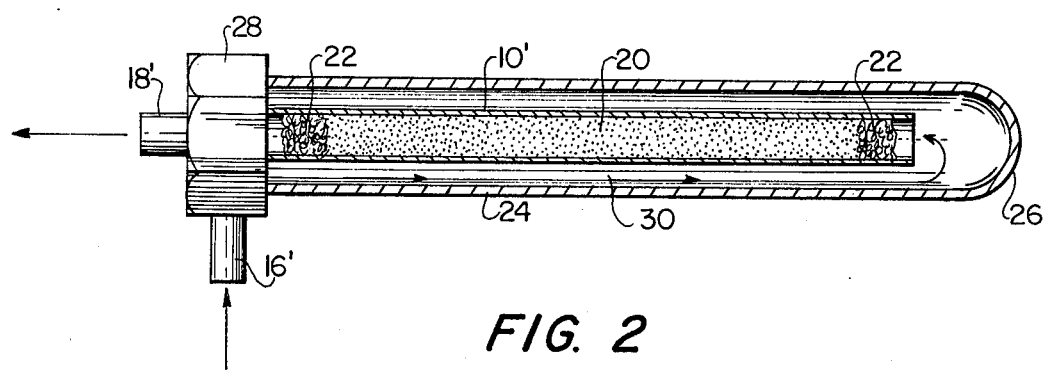
FIG. 2 is a longitudinal sectional view of another scrubbing device of the invention.

FIG. 2 illustrates a second example of the invention, wherein parts similar to those in FIG. 1 are designated by the same or primed reference numbers. Here a tube 10' containing a bed of silver sulfate crystals 20 retained by plugs 22 is itself contained within an outer tube 24 closed at one end 26. A single fitting 28 is provided at the other end for coupling the device to an inlet pipe 16' and an outlet pipe 18', which in this example are at the same end of the device. Gas supplied to inlet pipe 16' passes along an annular flow passage 30 between tubes 10' and 24. The gas stream then reverses direction, passes through tube 10' and out outlet pipe 18'. Fitting 28 of course isolates the spaces within the tubes at one end thereof.

In other examples of the invention, tube 10 or 10' is filled with silver nitrate crystals or silver iodide crystals. Mixtures of any of the named suitable scrubbing compounds or successive scrubber sections of different such compounds are not excluded from the broader aspects of the invention. The dimensions and other parameters referred to above are applicable to all of the examples although the lifetime may vary somewhat when silver nitrate or silver iodide is employed.

While it is not desired that the invention be restricted to a particular theory of operation, it is believed that the hydrogen sulfide is removed by sorption upon and reaction with the particulate bed material. Silver sulfate crystals are the preferred bed material, although silver nitrate and silver iodide also exhibit most of the properties deemed desirable for the invention. However, these compounds appear to be more affected by ozone (producing an instrument output peak when ozone is added which decays more slowly than is the case with silver sulfate) and appear to be more light-sensitive than silver sulfate.

While preferred embodiments of the invention have been shown and described, it will be apparent to those skilled in the art that changes can be made in these embodiments without departing from the principles and spirit of the invention, the scope of which is defined in the appended claims.

The invention claimed is:

1. A process for measuring sulfur dioxide pollution of ambient air without hydrogen sulfide interference and with minimal deleterious effects of ozone, comprising removing at least about 98% of hydrogen sulfide from an ambient air gas stream, while passing at least about 98% of sulfur dioxide in the gas stream, by passing the gas stream through a hydrogen sulfide scrubber containing a bed of silver sulfate without pretreatment of the gas stream or the bed by drying or heating, and then passing the gas stream from the scrubber to an instrument for measuring sulfur dioxide.

2. A process in accordance with claim 1, wherein the temperature of the gas stream is in the range of about 10°–40° C.

3. A process in accordance with claim 2, wherein the relative humidity of the gas stream is within the range of about 10–95%.

4. A process in accordance with claim 1, wherein the bed is in the form of crystals of about 10–30 mesh.

5. A process for measuring sulfur dioxide pollution of ambient air without hydrogen sulfide interference and with minimal deleterious effects of ozone, comprising removing at least about 98% of hydrogen sulfide from an ambient air gas stream, while passing at least about 98% of sulfur dioxide in the gas stream, by passing the gas stream through a hydrogen sulfide scrubber containing a bed of silver iodide without pretreatment of the gas stream or the bed by drying or heating, and then passing the gas stream from the scrubber to an instrument for measuring sulfur dioxide.

6. In a system for measuring sulfur dioxide pollution of ambient air without hydrogen sulfide interference and with minimal deleterious effects of ozone, the improvement comprising means for removing at least about 98% of hydrogen sulfide from an ambient air gas stream, while passing at least about 98% of sulfur dioxide in the gas stream, said means comprising a hydrogen sulfide scrubber containing a bed of silver sulfate through which the gas stream is passed without pretreatment of the gas stream or the bed by drying or heating, and means for passing the gas stream from the scrubber to an instrument for measuring sulfur dioxide.

7. A system in accordance with claim 6, wherein the bed comprises silver sulfate crystals.

8. A system in accordance with claim 7, wherein the scrubber comprises a tube containing the crystals and the crystals are retained in the tube between porous gas-dispersing plugs.

9. In a system for measuring sulfur dioxide pollution of ambient air without hydrogen sulfide interference and with minimal deleterious effects of ozone, the improvement comprising means for removing at least about 98% of hydrogen sulfide from an ambient air gas stream, while passing at least about 98% of sulfur dioxide in the gas stream, said means comprising a hydrogen sulfide scrubber containig a bed of silver iodide through which the gas stream is passed without pretreatment of the gas stream or the bed by drying or heating, and means for passing the gas stream from the scrubber to an instrument for measuring sulfur dioxide.

* * * * *